US006796994B2

(12) United States Patent
Ignatius et al.

(10) Patent No.: US 6,796,994 B2
(45) Date of Patent: Sep. 28, 2004

(54) DEVICE FOR THE TREATMENT OF MUCOSITIS

(75) Inventors: Ronald W. Ignatius, Barneveld, WI (US); Todd S. Martin, Dodgeville, WI (US); Charles Kirk, Middleton, WI (US)

(73) Assignee: Quantum Devices, Inc., Barneveld, WI (US)

( * ) Notice: Subject to any disclaimer, the term of this patent is extended or adjusted under 35 U.S.C. 154(b) by 0 days.

(21) Appl. No.: 10/077,917

(22) Filed: Feb. 18, 2002

(65) Prior Publication Data

US 2002/0120312 A1 Aug. 29, 2002

Related U.S. Application Data

(60) Provisional application No. 60/271,867, filed on Feb. 27, 2001.

(51) Int. Cl.[7] ................................................ A61N 5/06
(52) U.S. Cl. ............................................ 607/88; 607/89
(58) Field of Search ............................ 607/88–90; 606/9

(56) References Cited

U.S. PATENT DOCUMENTS

| | | | |
|---|---|---|---|
| 5,278,432 A | | 1/1994 | Ignatius et al. |
| 5,464,436 A | * | 11/1995 | Smith ............................. 606/9 |
| 5,616,140 A | * | 4/1997 | Prescott ......................... 606/9 |
| 5,660,461 A | | 8/1997 | Ignatius et al. |
| 5,728,090 A | | 3/1998 | Martin et al. |
| 6,063,108 A | * | 5/2000 | Salansky et al. ............... 606/9 |
| 6,514,242 B1 | * | 2/2003 | Vasily et al. ................... 606/9 |

FOREIGN PATENT DOCUMENTS

| | | |
|---|---|---|
| RU | 1076122 | 2/1984 |
| RU | 1789229 | 1/1993 |
| RU | 2053817 | 2/1996 |
| RU | 2106160 | 3/1998 |
| WO | WO94/15666 | * 7/1994 ................. 606/9 |
| WO | 9529645 | 11/1995 |

OTHER PUBLICATIONS

Quantum Devices specifications pulled from http://web.archive.org/web/20001204152800/http://www.quantumdev.com/.*

Natalie Pourreau–Schneider et al. Correspondence. Soft–Laser Therapy for Iatrogenic Mucositis in Cancer Patients Receiving High–Dose Fluorouracil: A Preliminary Report, pp. 358–359. Journal of the National Cancer Institute, vol. 84, No. 5, Mar. 4, 1992.

Tiina Karu, Basics of the Action of Monochromatic Visible and Near Infrared Radiation on Cells, pp. 1–21. The Science of Low–Power Laser Therapy. Copyright 1998. Gordon and Breach Science Publishers.

Tiina Karu, Instrumentation and Irradiation Procedure, pp. 41–49. The Science of Low–Power Laser Therapy. Copyright 1998. Gordon and Breach Science Publishers.

(List continued on next page.)

Primary Examiner—Roy D. Gibson
Assistant Examiner—Henry M Johnson, III
(74) Attorney, Agent, or Firm—Michael Best & Friedrich LLP

(57) ABSTRACT

Apparatus is provided for the treatment of a medical condition, such as mucositis in patients who are undergoing cancer treatment. The apparatus has several embodiments. In each embodiment, an array of optoelectronic devices, such as light-emitting diodes (LEDs), is used to provide a uniform emission of monochromatic light while producing a minimal amount of heat. The LEDs may be cooled in several ways. The treatments are typically of a very short duration. In several embodiments, selected portions of the patient are treated using a hand-held or stationary lamp. In other embodiments, the entire gastrointestinal tract may be treated simultaneously.

10 Claims, 7 Drawing Sheets

OTHER PUBLICATIONS

Tiina Karu, Primary and Secondary Mechanisms of the Action of Monochromatic Visible and Near Infrared Radiation on Cells, pp. 53–64. The Science of Low–Power Laser Therapy. Copyright 1998. Gordon and Breach Science Publishers.

Tiina Karu, What Can One Learn from Experiments on Cellular Level? The Science of Low–Power Laser Therapy. Copyright 1998. Gordon and Breach Science Publishers, pp. 261–267).

Tubers to Tumors. Space Product Development, NASA, Feb. 15, 1999.

The MCW/NASA Light–Emitting Diode Homepage (www.mcw.edu/whelan), NASA Marshall Space Flight Center—SBIR Program, Jul. 15, 1999.

Dan Drolette, LEDs in Space. Can Light Hasten Healing in Space. Biophotonics International, Sep./Oct. 2000.

NASA Space Technology Shines Light on Healing. Marshall Space Flight Center News Release 00–336, Dec. 18, 2000.

LEDs Lighting the Way for Cancer Treatment and Wound Healing, NASA, George C. Marshall Space Flight Center, 2000.

Griffin L. Kawanza, Light Technology Offers Hope for Healing. Kawanza Griffin L. Milwaukee Journal/Sentinel Jan. 15, 2001.

Whelan et al., NASA Light Emitting Diode Medical Applications From Deep Space to Deep Sea, Whelan et al. Space Technology & Applications International Forum, 2001.

Michael E. Long, Surviving in Space, National Geographic, Jan. 2001, pp. 14–29.

Biostimulatory Windows in Low Intensity Laser Activation: Lasers, Scanners and NASA's Light Emitting Diode Array System. Journal of Clinical Laser & Surgery.

* cited by examiner

DEVICE FOR THE TREATMENT OF MUCOSITIS

RELATED APPLICATIONS

Priority is claimed under 35 U.S.C. §119 to U.S. patent application Ser. No. 60/271,867 filed Feb. 27, 2001.

This invention was made with U.S. Government support under Contract NAS8-00008 awarded by the National Aeronautics and Space Administration. The U.S. Government has certain rights in this invention.

BACKGROUND OF THE INVENTION

This invention relates to a device for the treatment of mucositis. The device includes arrays of optoelectronic devices, such as light emitting diodes, that emit radiation suitable for the treatment of mucositis.

Mucositis is a common complication of chemotherapy and radiation therapy. Because many chemotherapeutic drugs, as well as radiation therapy, kill all rapidly dividing cells indiscriminately, the mucosal linings of the mouth and gastrointestinal tract are often damaged during the treatment. As a result of these gastrointestinal effects, patients often develop ulcers in their mouths (i.e., oral mucositis) and suffer from nausea and diarrhea. Oral mucositis is a significant risk for patients as it can impair the ability to eat and drink and poses a risk for infection. Often times the severity of oral mucositis causes the chemotherapy and radiation therapy to be terminated or severely limited.

One method of treating mucositis is hyperbaric-oxygen therapy. Hyperbaric-oxygen therapy is currently the standard of care for ischemic, hypoxic, infected, and otherwise slowly-healing problem wounds, such as the ulcers that result from oral mucositis. Hyperbaric-oxygen therapy increases cellular activities, such as collagen production and angiogenesis, leading to an increased rate of healing. Hyperbaric-oxygen therapy involves treatment sessions of approximately 90 minutes in a confined, high-pressure chamber.

Hyperbaric-oxygen therapy has several disadvantages. For example, there are instances in which a patient who may benefit from hyperbaric oxygen is unable or unwilling to be treated in a high-pressure chamber. These situations include lack of access to a facility equipped with hyperbaric oxygen, claustrophobia, and certain chronic medical conditions which would make hyperbaric-oxygen therapy contraindicated. In addition, the long duration of the hyperbaric-oxygen therapy makes its use problematic, especially for young children.

Another method of treating mucositis is photodynamic therapy (PDT) or biostimulation using monochromatic light. Biostimulation is a method of using monochromatic light to deliver photons to cytochromes in the mitochondria of cells. Cytochromes are light-sensitive organelles that act as an electron transport chain, converting energy derived from the oxidation of glucose into adenosine triphosphate (ATP)—the mitochondria's fuel. By directly stimulating cytochromes with monochromatic light, it is believed that more fuel is pumped into the mitochondria of cells, increasing the energy available to the cells. Increasing the energy available to the cell is believed to ultimately speed up healing.

By pumping more fuel into the mitochondria, biostimulation is believed to increase the respiratory metabolism of many types of cells. The monochromatic light provided by biostimulation is believed to be absorbed by the mitochondria of many types of cells where it stimulates energy metabolism in muscle and bone, as well as skin and subcutaneous tissue. Specifically, biostimulation is believed to result in fibroblast proliferation, attachment and synthesis of collagen, procollagen synthesis, macrophage stimulation, a greater rate of extracellular matrix production, and growth factor production. Specifically, the growth factors that are produced include keratinocyte growth factor (KGF), transforming growth factor (TGF), and platelet-derived growth factor (PDGF).

One method of providing biostimulation is the use of lasers. Lasers can provide monochromatic light for the stimulation of tissues resulting in increased cellular activity during the healing process. Specifically, these activities are believed to include fibroblast proliferation, growth factor synthesis, collagen production, and angiogenesis.

Using lasers to provide monochromatic light for biostimulation has several disadvantages. First, lasers are limited by their wavelength capabilities. Specifically, the combined wavelengths of light optimal for wound healing cannot be efficiently produced, because laser conversion to near-infrared wavelengths is inherently costly. Second, lasers are limited by their beam width. A limited beam width results in limitations in the size of the wounds which may be treated by lasers. Third, and most importantly, along with the production of monochromatic light, lasers produce a significant amount of heat. As a result of the production of heat, lasers cannot be used for extended treatment times or in applications in which the patient cannot tolerate heat.

SUMMARY OF THE INVENTION

The invention provides a device for treating a medical condition, such as mucositis, using an array of optoelectronic devices, such as light-emitting diodes (LEDs), to produce a uniform emission of monochromatic light with the production of a minimal amount of heat.

In one embodiment of the present invention, a device for treating mucositis includes a housing positioned adjacent to a patient and a plurality of optoelectronic devices positioned within the housing. The optoelectronic devices, such as LEDs, emit radiation suitable for the treatment of mucositis while emitting a minimal amount of heat. The device also includes a cooling system that cools the optoelectronic devices.

In another embodiment of the present invention, a device for treating a medical condition, such as mucositis, includes a gantry suitable for accommodating a patient, a housing positioned adjacent the gantry, and a track coupled to at least one of the gantry and the housing. An array of optoelectronic devices, such as LEDs, is coupled to the housing. The optoelectronic devices emit radiation suitable for treating a medical condition while emitting a minimal amount of heat. A cooling system cools the array of optoelectronic devices. At least one of the gantry and the housing moves along the track changing the relative position between the gantry and the housing so that the radiation emitted by the optoelectronic devices is directed towards the patient.

In still another embodiment of the present invention, a device for treating a medical condition includes a first housing unit and a second housing unit. A first array of optoelectronic devices is positioned within the first housing unit and a second array of optoelectronic devices is positioned within the second housing unit. The optoelectronic devices emit radiation suitable for treating a medical condition while emitting a minimal amount of heat. The first and second housing units are positioned adjacent to the patient, so that the radiation emitted from the optoelectronic devices substantially encircles the patient.

In still another embodiment of the present invention, the device for treating mucositis includes a plurality of modules. Each module includes at least one electrically and thermally conductive lead frame substrate having an upper surface and being adapted to act as a heat sink. Each module also includes at least one optoelectronic device electrically connected to the upper surface of the lead frame substrate. The optoelectronic devices emit radiation suitable for treating a medical condition while emitting a minimal amount of heat. Each module also includes at least one connector that is adapted to interconnect the module with at least one other module. The modules interconnect to form an array, and the array is positioned adjacent to the patient so that the radiation emitted by the optoelectronic devices is absorbed by the patient.

It is a feature and advantage of the invention to provide a device for treating a medical condition, such as mucositis, that produces long-wavelength, broad-spectrum, near-infrared light, enabling both deeper and wider penetrations than laser light.

It is another feature and advantage of the invention to provide a device for treating a medical condition that produces multiple wavelengths, and is arranged in large, flat arrays so as to address large, three-dimensional surfaces.

It is still another feature and advantage of the invention to provide a device for treating a medical condition that provides uniform, energy density to the patient.

It is still another feature and advantage of the invention to provide a device for treating a medical condition that produces a broad, uniform, light output while emitting a minimal amount of heat.

It is still another feature and advantage of the invention to provide a device for treating a medical condition that demands less power and costs less to manufacture than lasers.

These and other features and advantages of the present invention will be apparent to those skilled in the art from the following description of the preferred embodiments and the drawings, in which:

BRIEF DESCRIPTION OF THE PREFERRED EMBODIMENTS

In each of the preferred embodiments of the present invention, at least one optoelectronic device is used to produce monochromatic light for the treatment of a medical condition, such as mucositis. The optoelectronic devices are preferably substantially monochromatic, double-heterojunction, Gallium-Aluminum-Arsenide (GaAlAs) LEDs of the type manufactured by Showa Denkoa or Stanley, both of Japan, or by Hewlett-Packard of Palo Alto, Calif. The optoelectronic devices may be connected together in a manner described in U.S. Pat. No. 5,278,432 issued Jan. 11, 1994 to Ignatius et al., which is incorporated herein by reference.

Preferably, the LEDs emit radiation at approximately 688 nanometers (nM), which is believed to be the optimal single wavelength for treating mucositis. If LEDs having a peak output of 688 nm are not available, then LEDs having a peak output near 688 nm (e.g., 680 nm) may be used. Most preferably, the LEDs are arranged in an array with LEDs that emit radiation at a wavelength of approximately 680 nm, LEDs that emit radiation at a wavelength of approximately 730 nm, and LEDs that emit radiation at a wavelength of approximately 880 nm. The combination of radiation at wavelengths of approximately 680 nm, 730 nm, and 880 nm is believed to be the optimal combination of radiation for treating mucositis. Other wavelengths may also be suitable for treating mucositis or other medical conditions, such as approximately 670 nm +/−15 nm, 780 nm +/−15 nm, or 830 nm +/−15 nm. Moreover, as further research is conducted, other wavelengths may be found to be effective. However, the present invention is not limited to the use of any specific wavelength.

In addition to the wavelength of the radiation emitted by the LEDs, the following parameters should be considered to optimize the stimulative effect of the LEDs on biological tissues: the energy density required for activation $(E/a)_{act}$, the light intensity $I_{stim}$, and the total irradiation time $\Delta t_{tot}$. The parameters are interrelated according to the following equation, $$(E/a)_{act} = I_{stim} \times \Delta t_{tot}$$

where intensities necessary for stimulation $I_{stim}$ must surpass a threshold intensity $I_o$, i.e., $$I_{stim} \geq I_o$$

Light intensities lower than threshold values $I_o$ typically do not produce biostimulatory effects, even under prolonged irradiation times $\Delta t_{tot}$.

Figure 1:
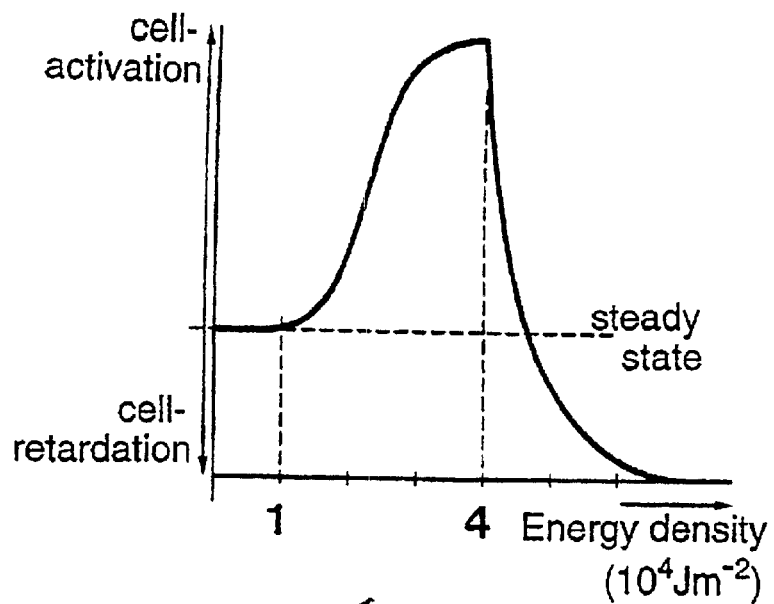
FIG. 1 is a graphical illustration of the optimal energy density for cell activation.

The optimal energy density for cellular activation $(E/a)_{act}$ has been determined to be approximately 4 Joules per centimeter squared, as illustrated in FIG. 1. The light intensity of the radiation emitted by the LEDs $I_{stim}$ is approximately 60 milli-Watts (mW) per centimeter squared, which is greater than $I_o$. Accordingly, the total irradiation time $\Delta t_{tot}$ necessary to irradiate the patient with 4 Joules per centimeter squared of energy is about 70 seconds. This short treatment time is particularly desirable with young children and other patients, because it reduces the patient's anxiety level.

Figure 2:
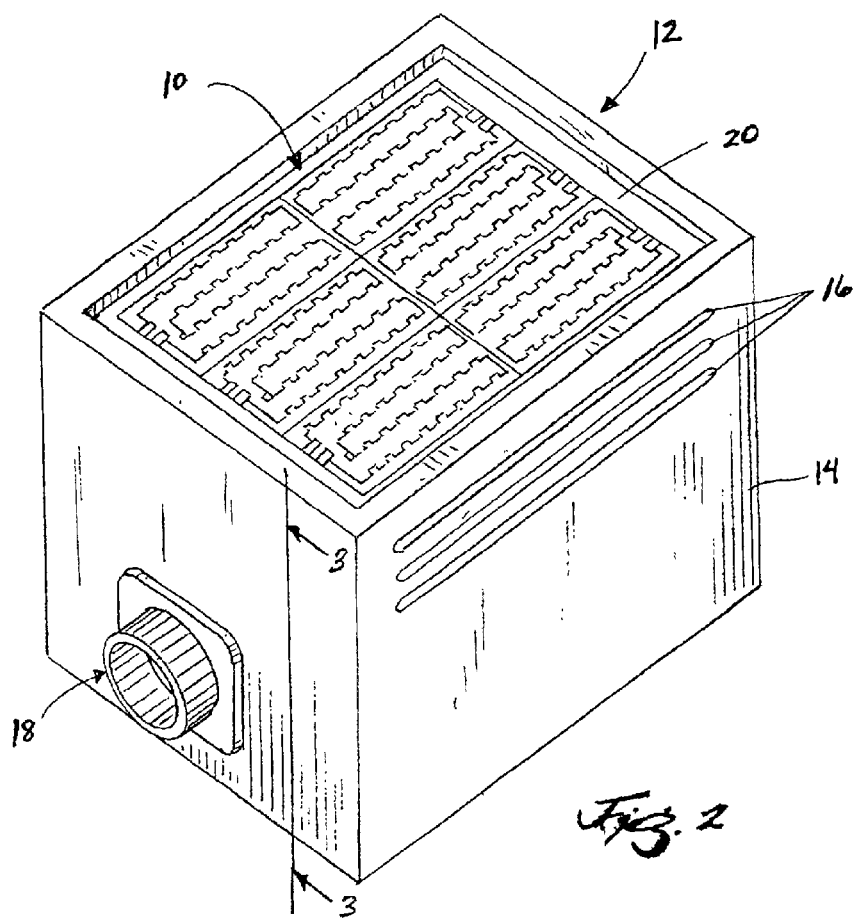
FIG. 2 is a perspective view of an embodiment of the present invention in the form of a modular housing.

Referring to FIG. 2, an array of LEDs 10 is positioned within a modular unit 12. The modular unit 12 of FIG. 2 is also disclosed in U.S. Pat. No. 5,278,432 issued Jan. 11, 1994 to Ignatius et al., and is incorporated by reference herein. The modular unit 12 includes a housing 14 that supports the LED array 10. Preferably, a plurality of air vents 16 are formed in at least one side of housing 14. The modular unit 12 also includes a connector 18 that is adapted to receive a power cord from a power supply unit (not shown). Preferably, modular unit 12 includes an unbreakable translucent cover plate 20 suitable to electrically isolate the patient from the LED array 10.

Figure 3:
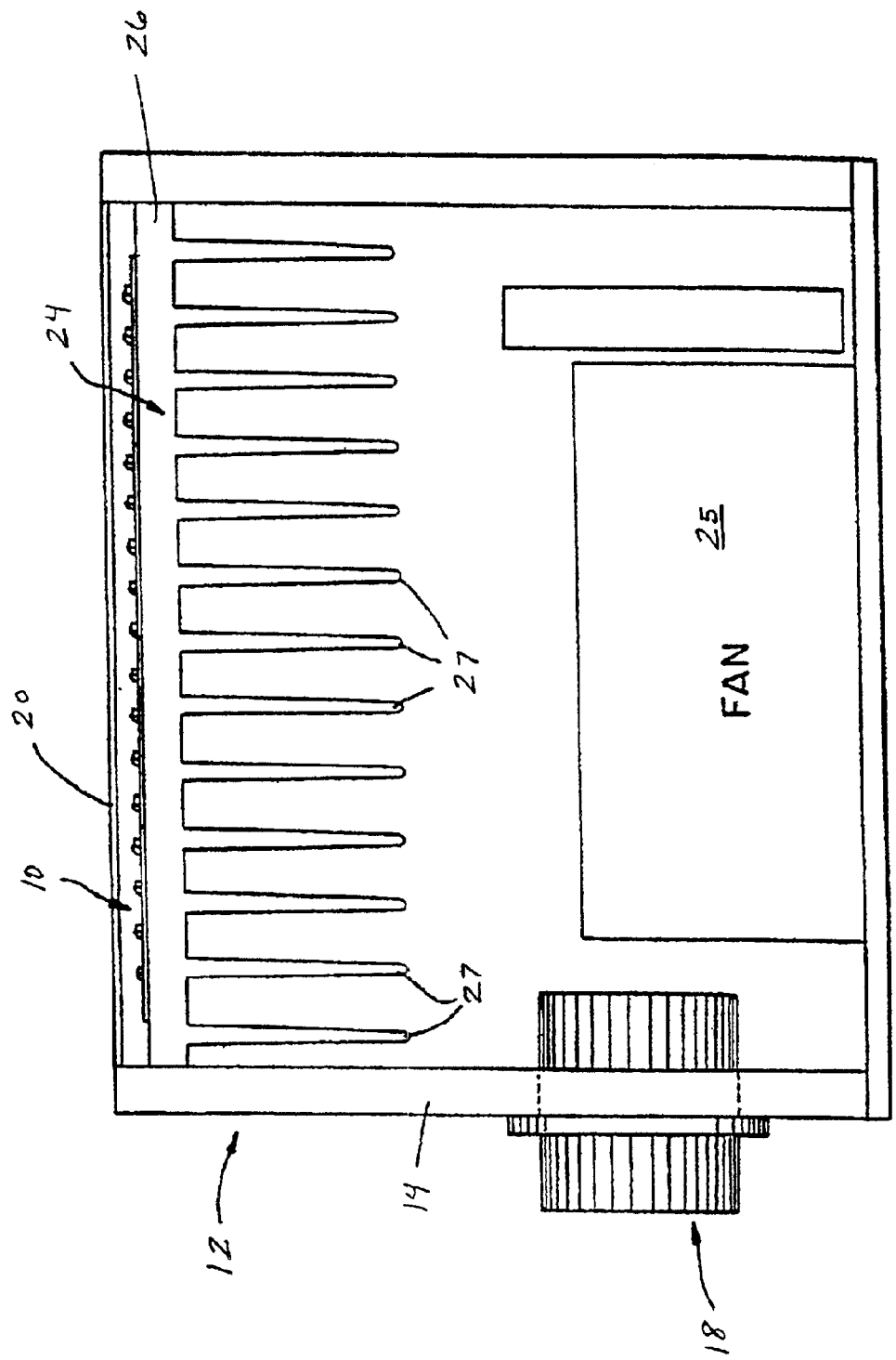
FIG. 3 is a cross-sectional view of the modular housing, taken along line 3—3 of FIG. 2.

Referring to FIG. 3, the modular unit 12 preferably includes a cooling system 24 in the form of a fan 25 and an internal heat sink 26 that has a plurality of fins or vanes 27 from which heat generated by the LED array 10 is dissipated.

Figure 4:
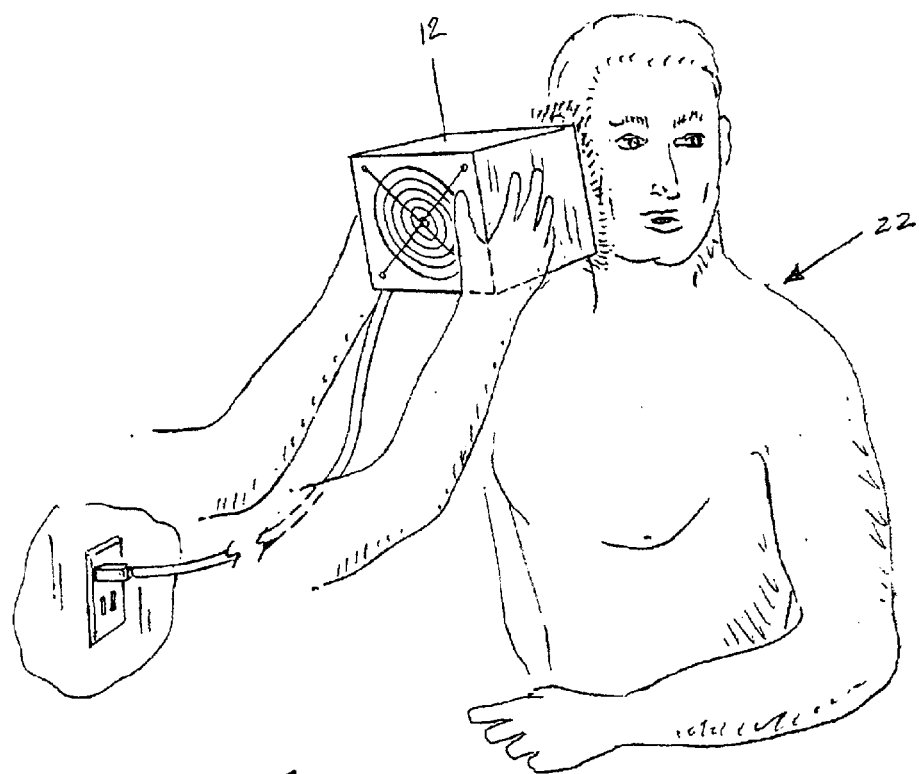
FIG. 4 is an illustration of the modular housing of FIG. 2 being used to treat oral mucositis.

FIG. 4 depicts the modular unit 12 positioned adjacent to the cheek of a patient 22 in order to treat oral mucositis.

Figure 5:
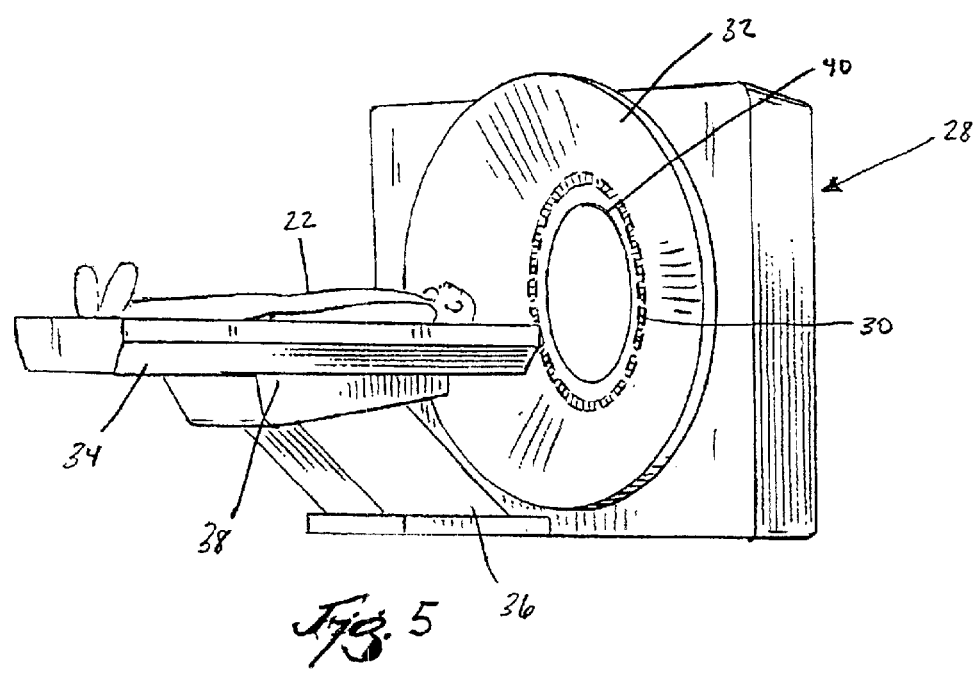
FIG. 5 is a perspective view of an embodiment of the present invention in the form of a radiation scanner.

Referring to FIG. 5, another embodiment of the present invention is in the form of a radiation scanner 28. The radiation scanner 28 includes an array of LEDs 30, a circular housing 32, a gantry 34, a base 36, and a track 38. The array of LEDs 30 is positioned within the circular housing 32. The array of LEDs 30 may include LEDs emitting radiation at a single wavelength, such as approximately 688 nm, or at a combination of wavelengths, such as approximately 670 nm, 680 nm, 730 nm, 780 nm, 830 nm, or 880 nm. The array of LEDs 30 is covered by a sheet 40 of translucent material (i.e., material that allows most or all radiation to be transmitted through it). Preferably, the circular housing 32 substantially encircles the gantry 34, which is suitable for the patient 22 to lie on. However, the housing 32 could also be in the form of a cantilever beam or a boom positioned adjacent to the gantry 34.

The gantry 34 is supported by the base 36. The base 36 includes the track 38, which preferably couples the gantry 34 to the base 36. Preferably, the gantry 34 moves along the track 38 to change the relative position between the gantry 34 and the circular housing 32. However, the circular housing 32 could also be coupled to a track for changing the relative position between the gantry 34 and the circular housing 32. Moreover, if the housing 32 is in the form of a cantilever beam or a boom, the cantilever beam or the boom could be coupled to a track for changing the relative position between the gantry 34 and the cantilever beam or the boom. As a result, the radiation emitted from the array of LEDs 30 is directed toward the patient 22 incrementally as the relative position between the gantry 34 and the circular housing 32 changes.

Figure 6:
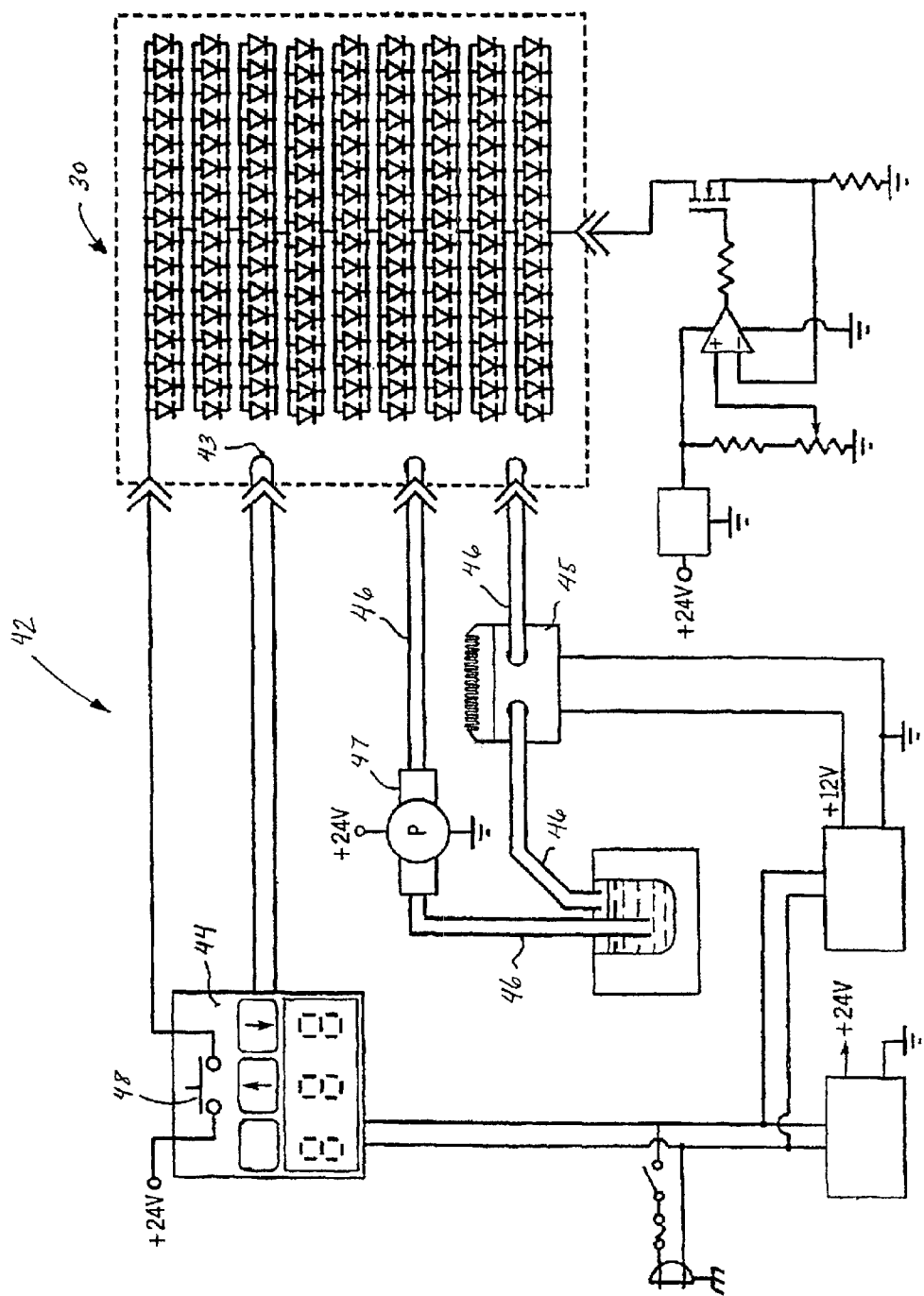
FIG. 6 is a schematic diagram of a liquid cooling system for use in various embodiments of the present invention.

Referring to FIG. 6, the circular housing 32 preferably includes a cooling system for cooling the array of LEDs 30. The cooling system is preferably in the form of at least one fan (not shown) or most preferably in the form of a liquid cooling system 42. Preferably, the liquid cooling system 42 includes a thermocouple 43, a temperature indicator and controller device 44, a liquid-to-air thermoelectric cooler 45, a plurality of passageways 46, and a pump 47.

The thermocouple 43 is coupled to the array of LEDs 30 and senses the temperature of the array of LEDs 30. The thermocouple 43 is also coupled to the temperature indicator and controller device 44. If the temperature of the array of LEDs 30 exceeds a preset level or a threshold temperature, such as 96° Fahrenheit, power to the array of LEDs 30 is interrupted by opening an interrupt switch 48 in the temperature indicator and controller device 44.

In addition to interrupting power to the array of LEDs 30, the thermoelectric cooler 45 provides cooling fluid to the array of LEDs 30 via the plurality of passageways 46. The cooling fluid is then pumped away from the array of LEDs through the plurality of passageways 46 via the pump 47.

Figure 7:
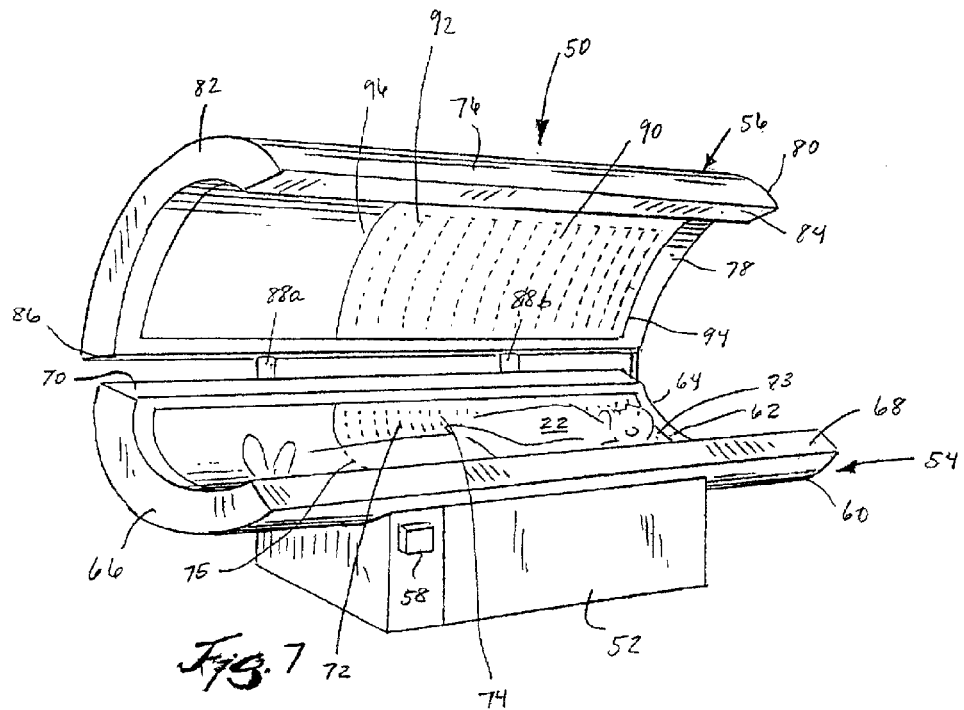
FIG. 7 is a perspective view of an embodiment of the present invention in the form of a radiation bed.

Referring to FIG. 7, another embodiment of the present invention is in the form of a radiation bed 50. The radiation bed 50 includes a base 52, a lower housing unit 54, and an upper housing unit 56. The base 52 supports the lower housing unit 54 and the upper housing unit 56. The base 52 can have any suitable configuration such as the configuration generally shown in FIG. 7 and houses the power supply (not shown) that is used to power arrays of LEDs in the lower housing unit 54 and the upper housing unit 56. A controller 58 can be attached to the base 52 to control the radiation bed 50.

The lower housing unit 54 has an outer wall 60, an inner wall 62, a pair of oppositely disposed ends 64 and 66, a first longitudinally extending edge 68, and a second longitudinally extending edge 70. The outer wall 60 is mounted directly to the base 52.

An array of LEDs 74 is preferably coupled to and supported by the outer wall 60 of the lower housing unit 54. The array of LEDs 74 can be coupled to the outer wall 60 in any manner so as to enable the radiation emitted from the LEDs to be directed toward the patient 22. The array of LEDs 74 may include LEDs emitting radiation at a single wavelength, such as approximately 688 nm, or at a combination of wavelengths, such as approximately 670 nm, 680 nm, 730 nm, 780 nm, 830 nm, or 880 nm. Preferably, the array of LEDs 74 extends from a first array end 73 to a second array end 75 and spans from the first longitudinally extending edge 68 to the second longitudinally extending edge 70. In this manner, the radiation emitted from the array of LEDs 74 is absorbed by the patient's head and torso, but not the patient's legs, in order to irradiate only the patient's gastrointestinal tract.

The inner wall 62 of the lower housing unit 54 includes an upwardly facing, concave sheet 72 of translucent material (i.e., material that allows most or all radiation to be transmitted through it). Preferably, the concave sheet 72 of translucent material extends from the first array end 73 to the second array end 75 and spans from the first longitudinally extending edge 68 to the second longitudinally extending edge 70, in order to provide a translucent covering for the array of LEDs 74. The radiation emitted by the array of LEDs 74 is transmitted through the concave sheet 72 toward the patient 22. Preferably, the concave sheet 72 of translucent material also electronically isolates the patient 22 from the array of LEDs 74.

The upper housing unit 56 has an outer wall 76, an inner wall 78, a pair of oppositely disposed ends 80 and 82, a first longitudinally extending edge 84, and a second longitudinally extending edge 86. The ends 80 and 82 and longitudinal edges 84 and 86 on the upper housing unit 56 have the same lengths as the corresponding ends 64 and 66 and longitudinal edges 68 and 70 on the lower housing unit 54.

The outer wall 76 is mounted to a pair of hinge arms 88a and 88b that allow the upper housing unit 56 to move between an open position and a closed position. The hinge arms 88a and 88b can be any devices that permit the upper housing unit 56 to move between an open and a closed position. The upper housing unit 56 can be connected to the base 52 using any conventional fastening device.

An array of LEDs 90 is preferably coupled to and supported by outer wall 76 of the upper housing unit 56. The array of LEDs 90 can be coupled to the outer wall 76 in any manner so as to enable the radiation emitted from the LEDs to be directed toward the patient 22. The array of LEDs 90 may include LEDs emitting radiation at a single wavelength, such as approximately 688 nm, or at a combination of wavelengths, such as approximately 670 nm, 680 nm, 730 nm, 780 nm, 830 nm, or 880 nm. Preferably, the array of LEDs 74 in the lower housing unit 54 and the array of LEDs 90 in the upper housing unit 56 include LEDs emitting radiation at the same wavelengths and in the same configuration. Preferably, the array of LEDs 90 extends from a first array end 94 to a second array end 96 and spans from first longitudinally extending edge 84 to second longitudinally extending edge 86. In this manner, the radiation emitted from the array of LEDs 90 is absorbed by the patient's head and torso, but not the patient's legs, in order to only irradiate the patient's gastrointestinal tract.

The inner wall 78 of the upper housing unit 56 includes a concave sheet 92 of translucent material. The radiation emitted by the array of LEDs 90 is transmitted through the concave sheet 92 toward the patient 22. Preferably, the concave sheet 92 of translucent material extends from a first array end 94 to a second array end 96 and spans from the first longitudinally extending edge 84 to the second longitudinally extending edge 86, in order to provide a translucent covering for the array of LEDs 90. The radiation emitted by the array of LEDs 90 is transmitted through the concave sheet 92 toward the patient 22. Preferably, the concave sheet 92 of translucent material also electronically isolates the patient from the array of LEDs 90.

The lower housing unit 54 and the upper housing unit 56 preferably include at least one cooling system for cooling the arrays of LEDs 74 and 90. Referring to FIG. 6, the cooling system is preferably in the form of at least one fan (not shown) or most preferably in the form of a liquid cooling system 42. Preferably, the liquid cooling system 42 includes a thermocouple 43, a temperature indicator and controller device 44, a liquid-to-air thermoelectric cooler 45, a plurality of passageways 46, and a pump 47.

The thermocouple 43 is coupled to the arrays of LEDs 74 and 90 and senses the temperature of the arrays of LEDs 74 and 90. The thermocouple 43 is also coupled to the temperature indicator and controller device 44. If the temperature of the arrays of LEDs 74 and 90 exceeds a preset level, such as 96° Fahrenheit, power to the arrays of LEDs 74 and 90 is interrupted by opening an interrupt switch 48 in the temperature indicator and controller device 44.

In addition to interrupting power to the arrays of LEDs 74 and 90, the thermoelectric cooler 45 provides cooling fluid to the arrays of LEDs 74 and 90 via the plurality of passageways 46. The cooling fluid is then pumped away from the array of LEDs through the plurality of passageways 46 via the pump 47.

Figure 8:
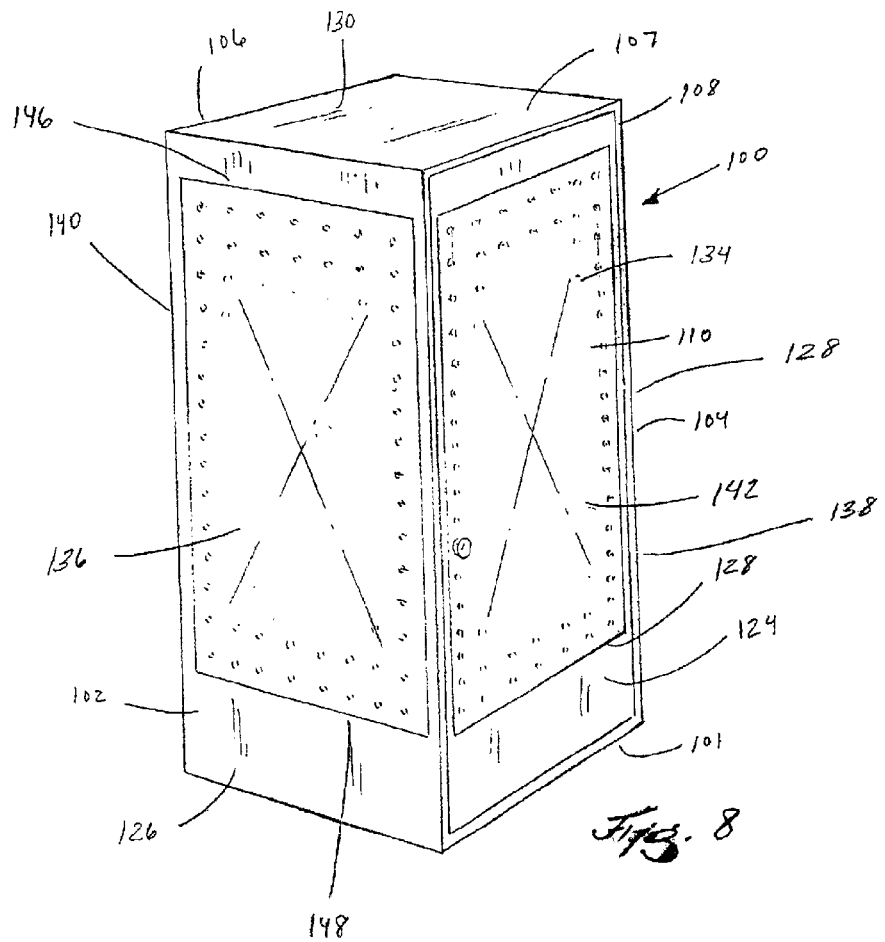
FIG. 8 is a perspective view of an embodiment of the present invention in the form of a radiation booth.

Referring to FIG. 8, another embodiment of the present invention is in the form of a radiation booth 100. The radiation booth 100 includes a base 101, a first side wall 102, a second side wall 104, a back wall 106, a top wall 107, a door frame 108, and a door 110. The base 101 is coupled to the side walls 102 and 104, to the back wall 106, to the top wall 107, and to the door frame 108 in any conventional manner in order to form a rectangular booth enclosure. The door 110 is coupled to the door frame 108 in any conventional manner to allow the door 110 to move between an open position and a closed position. Preferably, the door 110 is biased toward the closed position to help prevent radiation from escaping from the radiation booth 100.

The radiation booth 100 includes an interior enclosure 124 comprised of a first side wall interior surface 126, a second side wall interior surface 128, a back wall interior surface 130, and a door interior surface 134. A first array of LEDs 136 is coupled to the first side wall interior surface 126 in any conventional manner, as long as the radiation emitted by the LEDs is directed toward a patient standing within the interior enclosure 124. In a similar manner, a second array of LEDs 138 is coupled to the second side wall interior surface 128 20 and a third array of LEDs 140 is coupled to the back wall interior surface 130. A door LED array 142 is coupled to the door interior surface 134. The arrays of LEDs 136, 138, 140, and 142 each extend from an array top line 146 extending around the circumference of the upper portion of the interior enclosure 124 to an array bottom line 148 extending around the circumference of the lower portion of the interior enclosure 124. In this manner, radiation is directed toward the head and torso of the patient standing in the interior enclosure 124, but radiation is not directed toward the legs of the patient, in order to only irradiate the patient's gastrointestinal tract.

Preferably, the radiation booth 100 includes a cooling system for cooling the arrays of LEDs 136, 138, 140, and 142. Referring to FIG. 6, the cooling system is preferably in the form of at least one fan (not shown) or most preferably in the form of a liquid cooling system 42. Preferably, the liquid cooling system 42 includes a thermocouple 43, a temperature indicator and controller device 44, a liquid-to-air thermoelectric cooler 45, a plurality of passageways 46, and a pump 47.

The thermocouple 43 is coupled to the arrays of LEDs 136, 138, 140, and 142 in order to sense the temperature of the arrays of LEDs. The thermocouple 43 is also coupled to the temperature indicator and controller device 44. If the temperature of the arrays of LEDs exceeds a preset level, such as 96° Fahrenheit, power to the arrays of LEDs is interrupted by opening an interrupt switch 48 in the temperature indicator and controller device 44.

In addition to interrupting power to the arrays of LEDs, the thermoelectric cooler 45 provides cooling fluid to the arrays of LEDs via the plurality of passageways 46. The cooling fluid is then pumped away from the array of LEDs through the plurality of passageways 46 via the pump 47.

Figure 9:
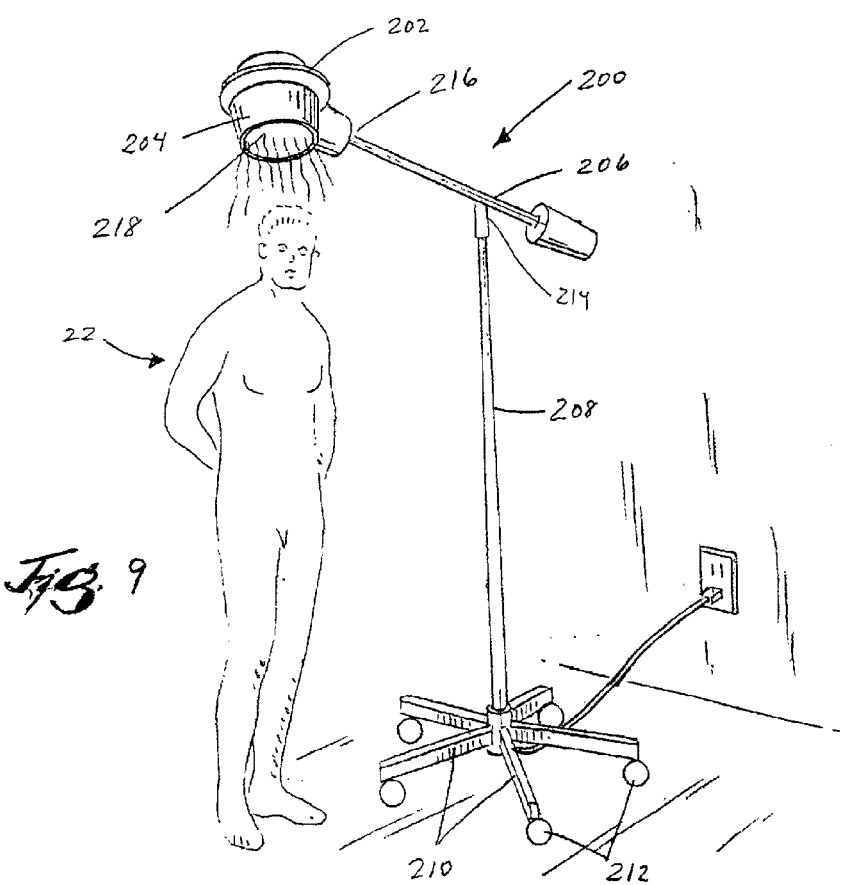
FIG. 9 is a perspective view of an embodiment of the present invention in the form of a mobile lamp.

Referring to FIG. 9, another embodiment of the present invention is in the form of a mobile lamp 200. The mobile lamp 200 includes a base 202, a reflector 204, a cross support member 206, a vertical support member 208, a plurality of horizontal support members 210, and a plurality of wheels 212. Each wheel 212 is rotatably coupled to one horizontal support member 210. Each of the horizontal support members 210 are coupled to the vertical support member 208 providing mobile support for the lamp 200. The vertical support member 208 is rotatably coupled to the cross support member 206 by a hinge 214. Preferably, the hinge 214 is rotatable into various positions and is capable of maintaining the position that it is rotated into. The cross support member 206 is rotatably coupled to the base 202 by a hinge 216. Preferably, the hinge 216 is rotatable into various positions and is capable of maintaining the position that it is rotated into in order to allow the base 202 to be aimed toward a patient 22. The base 202 is coupled to an array of LEDs 218. Preferably, the base 202 is also coupled to a reflector 204 which has a reflective surface to collimate any stray light from the array of LEDs 218 into substantially parallel rays toward the patient 22.

The array of LEDs 218 may be formed as discussed above in connection with FIGS. 2 and 3, or it may be formed from a plurality of modular units that are snapped together in a manner disclosed in U.S. Pat. No. 5,660,461 issued Aug. 26, 1997 to Ignatius et al., which is incorporated herein by reference. The modular units include electrically and thermally conductive lead frame substrates, optoelectronic devices coupled to the lead frame substrates, and reflectors that include male and female-type connectors used to interconnect with other modules. The positioning of the connectors on the reflectors allows for a wide variety of configurations for the completed array 218. Accordingly, although a circular base 202 and array 218 are illustrated in FIG. 9, the base and array may be rectangular, square, or any other suitable shape. Preferably, the shape of each of the lead frame substrates provides enough surface area for heat dissipation without the need for an additional cooling apparatus. If no additional cooling apparatus is used, it may be necessary to extend the treatment duration since the LEDs typically cannot be driven as hard in this configuration.

Figure 10:
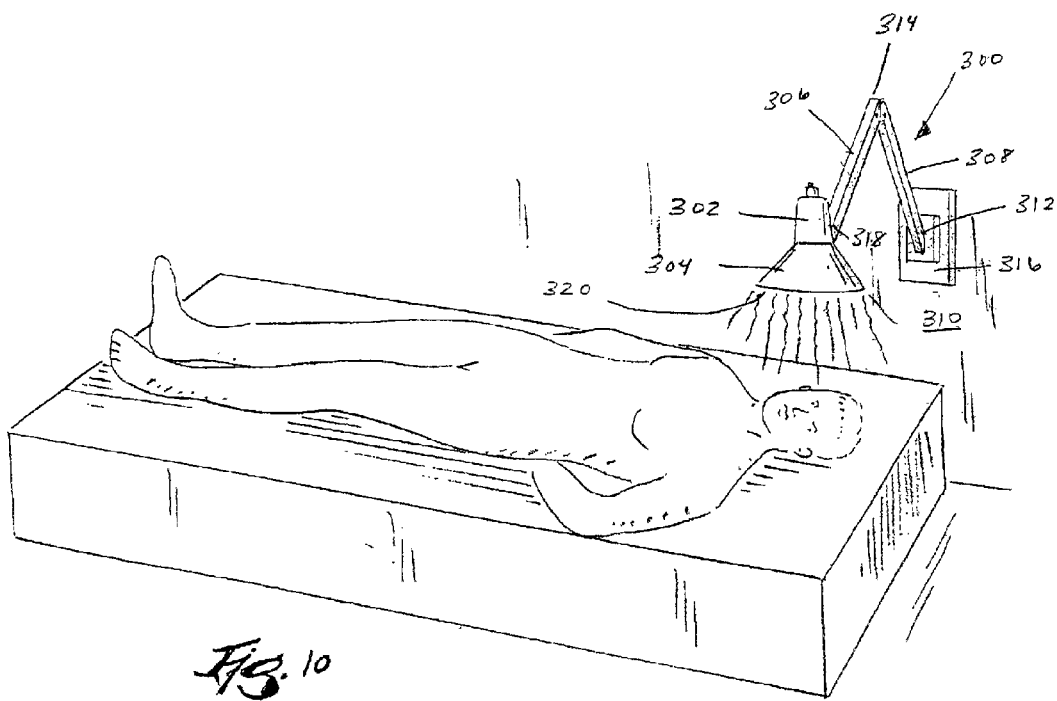
FIG. 10 is a perspective view of an embodiment of the present invention in the form of a stationary lamp.

Referring to FIG. 10, another embodiment of the present invention is in the form of a stationary lamp 300. The stationary lamp 300 includes a base 302, a reflector 304, a first support member 306, a second support member 308, a mounting bracket 316, and an array of LEDs 320. Preferably, the mounting bracket 316 is coupled to a wall 310. The second support member 308 is rotatably coupled to the mounting bracket 316 by a hinge 312. The first support member 306 is rotatably coupled to the second support member 308 by a hinge 314. The base 302 is coupled to the first support member 306 by a hinge 318. Each of the hinges 312, 314, and 318 are rotatable into various positions and are capable of maintaining the position that they are rotated into. The array of LEDs 320 is coupled to the base 302. The array of LEDs 320 may be formed as discussed above in connection with FIGS. 2 and 3, or it may be formed from a plurality of modular units that are snapped together in a manner disclosed in U.S. Pat. No. 5,660,461 issued Aug. 26, 1997 to Ignatius et al. Preferably, the base 302 is also coupled to a reflector 304 which has a reflective surface to collimate any stray light from the LEDs into substantially parallel rays toward the patient 22.

Preferably, the array of LEDs 320 is formed from a plurality of modular units that are snapped together in a manner disclosed in U.S. Pat. No. 5,660,461 issued Aug. 26, 1997 to Ignatius et al., which is incorporated herein by reference. The modular units include electrically and thermally conductive lead frame substrates, optoelectronic devices coupled to the lead frame substrates, and reflectors that include male and female-type connectors used to interconnect with other modules. The positioning of the connectors on the reflectors allows for a wide variety of configurations for the completed array 320. Accordingly, although a circular base 302 and array 320 are illustrated in FIG. 10, the base and array may be rectangular, square, or any other suitable shape. Preferably, the shape of each of the lead frame substrates provides enough surface area for heat dissipation without the need for an additional cooling apparatus. If no additional cooling apparatus is used, it may be necessary to extend the treatment duration since the LEDs typically cannot be driven as hard in this configuration.

Figure 12:
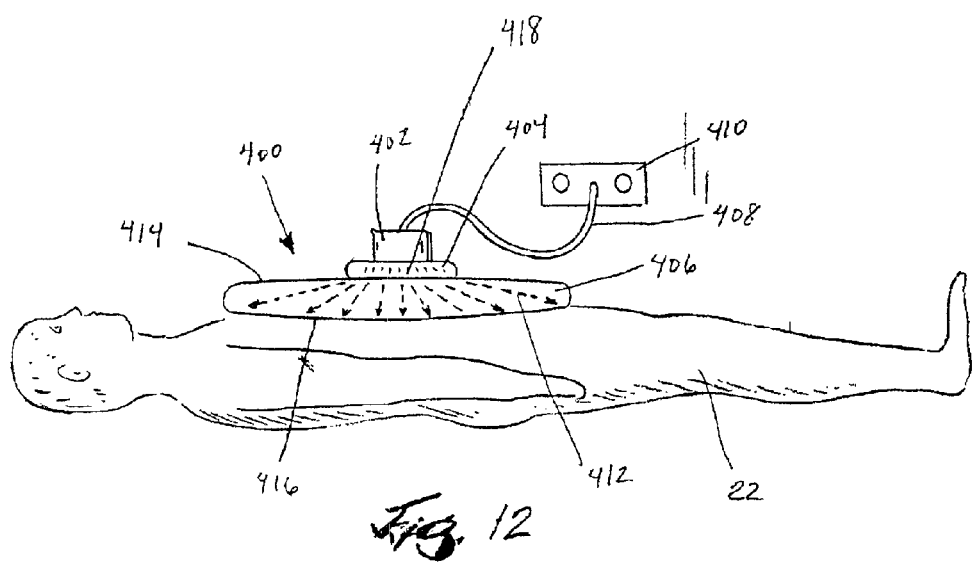
FIG. 12 is a side view of the radiation blanket of FIG. 11.
Figure 11:
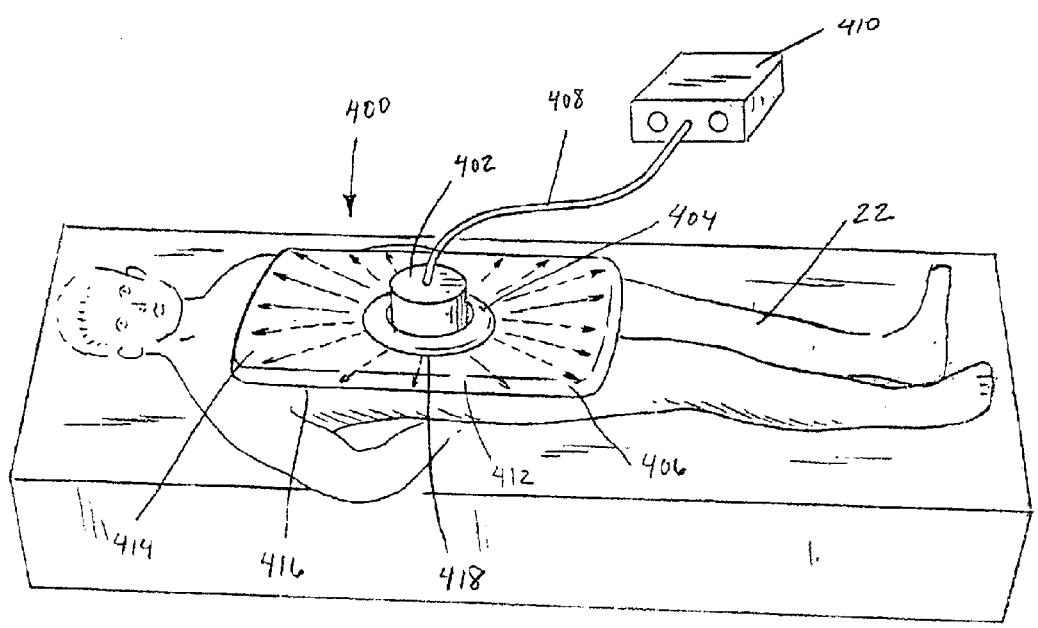
FIG. 11 is a perspective view of an embodiment of the present invention in the form of a radiation blanket.

Referring to FIGS. 11 and 12, another embodiment of the present invention is in the form of a radiation blanket 400. The radiation blanket 400 includes modular unit 402, a seal 404, a blanket membrane 406, an electrical connector 408, a power source 410, and an array of LEDs 418. The array of LEDs 418 is coupled to the modular unit 402 which may be constructed in the same manner as the modular units disclosed in U.S. Pat. No. 5,278,432 issued Jan. 11, 1994 to Ignatius et al., which is incorporated herein by reference. Of course, other types of LED arrays could be used. Seal 404 couples the modular unit 402 to the blanket membrane 406.

Preferably, the blanket membrane 406 is a balloon-like membrane in a size and shape suitable to cover a patient 22 from approximately the patient's neck to approximately the patient's groin in order to irradiate the patient's entire gastrointestinal tract. The blanket membrane 406 is preferably made of a flexible material, such as nylon, and contains a diffuser fluid 412 which is preferably in the form of a lipid solution. As best shown in FIG. 12, the blanket membrane 406 includes a top membrane 414 coupled to a bottom membrane 416. The diffuser fluid 412 is contained between the top membrane 414 and the bottom membrane 416. Preferably, the diffuser fluid 412 is contained between the top membrane 414 and the bottom membrane 416 in the form of a substantially even sheet of fluid. The top membrane 414 is preferably a non-translucent, flexible material, while the bottom membrane is preferably a translucent, flexible material. LED radiation from the array of LEDs 418 diffuses through the diffuser fluid 412 and through the translucent bottom membrane 416 of the blanket membrane 406 in order to impart radiation to the patient 22.

The modular unit 402 of the radiation blanket 400 is preferably cooled via a fan 25 and an internal heat sink 26 (as shown in FIG. 3). The internal heat sink 26 has a plurality of fins or vanes 27 from which heat generated by the array of LEDs 418 is dissipated. Preferably, the modular unit 402 includes a plurality of air vents 16 (as shown in FIG. 2) in at least one side of the housing of the modular unit 402.

According to the method of the invention, one of the embodiment devices is positioned adjacent to the patient or the patient is positioned adjacent to one of the embodiment devices in a manner that allows the patient to absorb LED radiation. As one example, the modular unit 12 is positioned adjacent to the patient's cheek. In other examples, the patient lies down in the radiation bed 50 or enters and stands up-right in the radiation booth 100. Once the patient is positioned in a manner that allows the patient to absorb LED radiation, the patient is irradiated with LED radiation for a predetermined time period. Most preferably, the patient is irradiated for 70 seconds at a power density of 4 Joules per centimeter squared. However, the patient may be irradiated for shorter or longer periods of time at lesser or greater power densities. Preferably, the patient is irradiated up to once per day, five days per week, until the mucositis symptoms have substantially diminished.

Although several embodiments of the present invention have been shown and described, alternate embodiments will be apparent to those skilled in the art and are within the intended scope of the present invention. Therefore, the invention is to be limited only by the following claims.

What is claimed is:

1. A device for treating mucositis in a patient, the device comprising:
   a housing adapted to be positioned adjacent to the patient;
   a plurality of optoelectronic devices positioned within the housing, the optoelectronic devices emitting radiation having an energy intensity of approximately 60 mW per centimeter squared, the optoelectronic devices emitting radiation at a wavelength suitable for the treatment of mucositis while emitting a minimal amount of heat; and
   a cooling system that cools the optoelectronic devices.

2. The device of claim 1, wherein the plurality of optoelectronic devices include a plurality of light-emitting diodes.

3. The device of claim 1, wherein the plurality of optoelectronic devices are positioned within the housing in an array, and wherein the array includes optoelectronic devices emitting radiation at a wavelength of at least one of approximately 670 nanometers, 680 nanometers, 730 nanometers, 780 nanometers, 830 nanometers, and 880 nanometers.

4. The device of claim 1, wherein the plurality of optoelectronic devices emit radiation at a wavelength of approximately 688 nanometers.

5. The device of claim 1, wherein a translucent cover plate is disposed between the housing and the plurality of optoelectronic devices to electrically isolate the patient from the plurality of optoelectronic devices.

6. The device of claim 1, wherein the cooling system includes a plurality of air vents in the housing and an internal heat sink positioned within the housing.

7. The device of claim 1, wherein the device is a mobile lamp.

8. The device of claim 1, further comprising a timer adapted to set exposure time.

9. A device for treating mucositis in a patient, the device comprising:

a housing adapted to be positioned adjacent to the patient;

a plurality of optoelectronic devices positioned within the housing, the optoelectronic devices emitting radiation at a wavelength suitable for the treatment of mucositis while emitting a minimal amount of heat;

a cover plate positioned over the plurality of optoelectronic devices in order to electrically isolate the patient from the plurality of optoelectronic devices; and a controller positioned within the housing and coupled to the plurality of optoelectronic devices, the controller adapted to provide power to the plurality of optoelectronic devices and a timer for setting a radiation timer period suitable for the treatment of mucositis.

10. The device of claim 9, wherein the controller provides power to the plurality of optoelectronic devices for a radiation time period of approximately 70 seconds.

* * * * *